(12) United States Patent  (10) Patent No.: US 8,431,154 B2
Dietrich et al.  (45) Date of Patent: *Apr. 30, 2013

(54) ORAL DOSAGE FORM CONTAINING A PDE 4 INHIBITOR AS AN ACTIVE INGREDIENT AND POLYVINYLPYRROLIDONE AS EXCIPIENT

(75) Inventors: Rango Dietrich, Constance (DE); Klaus Eistetter, Constance (DE); Hartmut Ney, Constance (DE)

(73) Assignee: Takeda GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/008,842

(22) Filed: Jan. 18, 2011

(65) Prior Publication Data

US 2011/0251244 A1  Oct. 13, 2011

Related U.S. Application Data

(63) Continuation of application No. 10/505,138, filed as application No. PCT/EP03/01650 on Feb. 19, 2003, now Pat. No. 7,951,397.

(30) Foreign Application Priority Data

Feb. 20, 2002 (DE) .................................. 102 07 160
Feb. 20, 2002 (EP) ..................................... 02003811

(51) Int. Cl.
*A61K 9/20* (2006.01)
(52) U.S. Cl.
USPC ....................................................... 424/464

(58) Field of Classification Search ........................ None
See application file for complete search history.

(56) References Cited

U.S. PATENT DOCUMENTS

| 3,065,142 A | 11/1962 | Antonides |
| 4,006,227 A | 2/1977 | Gallegos et al. |
| 4,024,240 A | 5/1977 | Thakkar |
| 4,343,804 A | 8/1982 | Munson et al. |
| 4,349,563 A | 9/1982 | Gilbert et al. |
| 4,450,164 A | 5/1984 | Bristol et al. |
| 4,464,372 A | 8/1984 | Bristol et al. |
| 4,563,455 A | 1/1986 | Ueda et al. |
| 4,621,084 A | 11/1986 | Takaya et al. |
| 4,686,227 A | 8/1987 | Ueda et al. |
| 4,725,601 A | 2/1988 | Ueda et al. |
| 4,753,945 A | 6/1988 | Gilbard et al. |
| 4,769,384 A | 9/1988 | Kise et al. |
| 4,782,055 A | 11/1988 | Ueda et al. |

(Continued)

FOREIGN PATENT DOCUMENTS

| CA | 2497176 | 3/2004 |
| CN | 1126468 C | 11/2003 |

(Continued)

OTHER PUBLICATIONS

Remington: The Science and Practice of Pharmacy, vol. II, 1995, pp. 1618-1628.*

(Continued)

*Primary Examiner* — Paul Dickinson
(74) *Attorney, Agent, or Firm* — Fish & Richardson P.C.

(57) ABSTRACT

Dosage forms for oral administration of a PDE 4 inhibitor whose solubility is slight are described. They contain PVP as binder.

38 Claims, 1 Drawing Sheet

U.S. PATENT DOCUMENTS

| | | | |
|---|---|---|---|
| 4,791,117 A | 12/1988 | Press | |
| 4,806,550 A | 2/1989 | Ife et al. | |
| 4,831,041 A | 5/1989 | Shiokawa et al. | |
| 4,833,149 A | 5/1989 | Press | |
| 4,839,353 A | 6/1989 | Hosoi et al. | |
| 4,900,775 A | 2/1990 | Smith et al. | |
| 4,920,129 A | 4/1990 | Shiokawa et al. | |
| 5,006,595 A | 4/1991 | Smith et al. | |
| 5,011,843 A | 4/1991 | Shell | |
| 5,041,442 A | 8/1991 | Romero et al. | |
| 5,051,508 A | 9/1991 | Brown et al. | |
| 5,089,504 A | 2/1992 | Ife et al. | |
| 5,102,892 A | 4/1992 | Geiss et al. | |
| 5,112,834 A | 5/1992 | Senn | |
| 5,188,838 A | 2/1993 | Deleuil et al. | |
| 5,200,417 A | 4/1993 | Brown et al. | |
| 5,215,999 A | 6/1993 | Uchida et al. | |
| 5,252,580 A | 10/1993 | Takahashi et al. | |
| 5,262,171 A * | 11/1993 | Login et al. | 424/465 |
| 5,286,494 A | 2/1994 | Fechner et al. | |
| 5,320,848 A | 6/1994 | Geyer et al. | |
| 5,326,879 A | 7/1994 | Takahashi et al. | |
| 5,340,827 A | 8/1994 | Beeley et al. | |
| 5,380,532 A | 1/1995 | Deleuil et al. | |
| 5,409,943 A | 4/1995 | Ife et al. | |
| 5,429,824 A | 7/1995 | June | |
| 5,439,917 A | 8/1995 | Briving et al. | |
| 5,534,515 A | 7/1996 | Grundler | |
| 5,665,730 A | 9/1997 | Senn et al. | |
| 5,677,302 A | 10/1997 | Karimian et al. | |
| 5,686,458 A | 11/1997 | Lee et al. | |
| 5,698,711 A | 12/1997 | Palfreyman | |
| 5,712,298 A | 1/1998 | Amschler | |
| 5,719,161 A | 2/1998 | Rainer | |
| 5,762,953 A | 6/1998 | Venkateshwaran | |
| 5,824,687 A | 10/1998 | Senn | |
| 5,891,904 A | 4/1999 | Stief et al. | |
| 5,972,381 A | 10/1999 | Sangekar et al. | |
| 5,972,927 A | 10/1999 | Pascal et al. | |
| 6,114,537 A | 9/2000 | Karimian et al. | |
| 6,124,313 A | 9/2000 | Grundler et al. | |
| 6,132,770 A | 10/2000 | Lundberg | |
| 6,160,119 A | 12/2000 | Senn | |
| 6,174,878 B1 | 1/2001 | Gamache et al. | |
| 6,218,400 B1 | 4/2001 | Daugan et al. | |
| 6,231,885 B1 | 5/2001 | Carrara | |
| 6,255,326 B1 | 7/2001 | Ashton et al. | |
| 6,258,833 B1 | 7/2001 | Martins et al. | |
| 6,265,415 B1 | 7/2001 | Amin et al. | |
| 6,270,807 B1 | 8/2001 | Danielson et al. | |
| 6,288,118 B1 | 9/2001 | Nieman et al. | |
| 6,313,136 B1 | 11/2001 | Amin et al. | |
| 6,313,137 B1 | 11/2001 | Amin et al. | |
| 6,328,993 B1 | 12/2001 | Linder et al. | |
| 6,348,602 B1 | 2/2002 | Fowler et al. | |
| 6,375,968 B1 | 4/2002 | Quong | |
| 6,379,682 B1 | 4/2002 | Tchinnis et al. | |
| 6,383,510 B1 | 5/2002 | Linder et al. | |
| 6,384,048 B1 | 5/2002 | Senn | |
| 6,432,451 B1 | 8/2002 | Lee et al. | |
| 6,436,953 B1 | 8/2002 | Senn | |
| 6,436,970 B1 | 8/2002 | Häfner et al. | |
| 6,448,274 B2 | 9/2002 | Friesen et al. | |
| 6,498,173 B1 | 12/2002 | Kilian | |
| 6,503,923 B1 | 1/2003 | Senn | |
| 6,531,493 B1 | 3/2003 | Kley et al. | |
| 6,537,983 B1 | 3/2003 | Biggadike et al. | |
| 6,555,583 B2 | 4/2003 | Nieman et al. | |
| 6,579,884 B1 | 6/2003 | Amin et al. | |
| 6,613,775 B1 | 9/2003 | Amin et al. | |
| 6,624,181 B1 | 9/2003 | Kilian et al. | |
| 6,630,161 B1 | 10/2003 | Leesman | |
| 6,670,394 B1 | 12/2003 | Christensen et al. | |
| 6,677,362 B1 * | 1/2004 | Ghebre-Sellassie et al. | 514/369 |
| 6,743,443 B1 | 6/2004 | Furitsu et al. | |
| 6,767,557 B2 | 7/2004 | Ulrich et al. | |
| 6,822,114 B1 | 11/2004 | Williams et al. | |
| 6,872,382 B1 | 3/2005 | Gamache et al. | |
| 6,897,229 B2 | 5/2005 | Kilian | |
| 7,056,936 B2 | 6/2006 | Kilian et al. | |
| 7,147,869 B2 | 12/2006 | Dietrich et al. | |
| 7,175,854 B2 | 2/2007 | Dietrich et al. | |
| 7,182,958 B1 | 2/2007 | Oren et al. | |
| 7,357,943 B2 | 4/2008 | Linder et al. | |
| 7,393,860 B1 | 7/2008 | Senn-Bilfinger | |
| 7,745,646 B2 | 6/2010 | Govek et al. | |
| 7,785,630 B2 | 8/2010 | Dietrich et al. | |
| 7,790,198 B2 | 9/2010 | Dietrich et al. | |
| 7,794,752 B1 | 9/2010 | Dietrich et al. | |
| 7,927,623 B2 | 4/2011 | Sugimoto et al. | |
| 7,951,397 B2 | 5/2011 | Dietrich et al. | |
| 7,951,398 B2 | 5/2011 | Dietrich et al. | |
| 2001/0044409 A1 | 11/2001 | Ghebre et al. | |
| 2002/0002191 A1 | 1/2002 | Friesen | |
| 2002/0086039 A1 | 7/2002 | Lee et al. | |
| 2002/0193393 A1 | 12/2002 | Pairet et al. | |
| 2003/0018071 A1 * | 1/2003 | Rennard et al. | 514/521 |
| 2003/0092706 A1 | 5/2003 | Barsig | |
| 2003/0099700 A1 | 5/2003 | Faham et al. | |
| 2003/0195233 A1 | 10/2003 | Magee | |
| 2003/0207845 A1 | 11/2003 | Keating et al. | |
| 2003/0212112 A1 | 11/2003 | Murdoch et al. | |
| 2004/0024007 A1 | 2/2004 | Pairet et al. | |
| 2004/0058896 A1 | 3/2004 | Dietrich et al. | |
| 2004/0058950 A1 | 3/2004 | Meade et al. | |
| 2004/0101558 A1 | 5/2004 | Dietrich et al. | |
| 2004/0151722 A1 | 8/2004 | Banerjee et al. | |
| 2004/0241235 A1 | 12/2004 | Lebon et al. | |
| 2005/0159492 A1 | 7/2005 | Dietrich et al. | |
| 2006/0069155 A1 | 3/2006 | Edelson | |
| 2006/0084684 A1 | 4/2006 | Bolle et al. | |
| 2006/0084685 A1 | 4/2006 | Koenen et al. | |
| 2006/0105038 A1 | 5/2006 | Lai et al. | |
| 2006/0142308 A1 | 6/2006 | Kolassa et al. | |
| 2006/0147382 A1 | 7/2006 | Bundschuh et al. | |
| 2006/0159758 A1 | 7/2006 | Gandhi et al. | |
| 2006/0198889 A1 | 9/2006 | Sandhu et al. | |
| 2006/0199865 A1 | 9/2006 | Beume et al. | |
| 2006/0228410 A1 | 10/2006 | Dumont et al. | |
| 2007/0122474 A1 | 5/2007 | Dietrich et al. | |
| 2007/0134729 A1 | 6/2007 | Christensen et al. | |
| 2007/0254928 A1 | 11/2007 | Wollin et al. | |
| 2008/0193544 A1 | 8/2008 | Bruck-Scheffler et al. | |
| 2008/0280958 A1 | 11/2008 | Bolle et al. | |
| 2010/0310477 A1 | 12/2010 | Pairet et al. | |
| 2011/0060016 A1 | 3/2011 | Dietrich et al. | |
| 2011/0212182 A1 | 9/2011 | Lebon et al. | |
| 2011/0251244 A1 | 10/2011 | Dietrich et al. | |
| 2011/0313005 A1 | 12/2011 | Bolle et al. | |

FOREIGN PATENT DOCUMENTS

| | | |
|---|---|---|
| CN | 1189832 C | 2/2005 |
| DE | 3011490 A1 | 3/1981 |
| DE | 3622036 A1 | 1/1987 |
| DE | 3917232 A1 | 11/1990 |
| DE | 3943385 A1 | 7/1991 |
| DE | 69101493 T2 | 8/1994 |
| DE | 10061137 A1 | 6/2002 |
| DE | 19925710 C2 | 10/2002 |
| EP | 33094 A1 | 8/1981 |
| EP | 68378 A1 | 1/1983 |
| EP | 120589 | 10/1984 |
| EP | 125756 A2 | 11/1984 |
| EP | 165545 A2 | 12/1985 |
| EP | 228006 A1 | 7/1987 |
| EP | 261912 A2 | 3/1988 |
| EP | 264883 A2 | 4/1988 |
| EP | 266890 A1 | 5/1988 |
| EP | 268989 A1 | 6/1988 |
| EP | 308917 A2 | 3/1989 |
| EP | 163965 | 11/1989 |
| EP | 368158 A1 | 5/1990 |
| EP | 120352 | 6/1990 |
| EP | 438359 A1 | 7/1991 |
| EP | 399267 A3 | 12/1991 |
| EP | 204285 B1 | 1/1992 |
| EP | 259174 B1 | 3/1992 |

| | | | |
|---|---|---|---|
| EP | 307078 B1 | 8/1992 |
| EP | 509974 A1 | 10/1992 |
| EP | 510562 | 10/1992 |
| EP | 330485 B1 | 5/1993 |
| EP | 563024 A1 | 9/1993 |
| EP | 387821 B1 | 8/1994 |
| EP | 393926 B1 | 9/1994 |
| EP | 617612 A1 | 10/1994 |
| EP | 537532 B1 | 11/1996 |
| EP | 535529 B1 | 7/1997 |
| EP | 1118615 A1 | 7/2001 |
| EP | 1161950 A1 | 12/2001 |
| EP | 1187601 A1 | 3/2002 |
| EP | 1105390 B1 | 6/2003 |
| EP | 1199074 | 4/2004 |
| EP | 1366760 A4 | 9/2005 |
| EP | 1120120 A4 | 4/2009 |
| EP | 1478399 | 3/2012 |
| ES | 2176252 T3 | 12/2002 |
| JP | 61205208 A | 9/1986 |
| JP | 2270873 A | 11/1990 |
| JP | 2049720 Y2 | 12/1990 |
| JP | 3284622 A | 12/1991 |
| JP | 3284686 A | 12/1991 |
| JP | 4212359 A | 8/1992 |
| JP | 5271070 A | 10/1993 |
| JP | 03031280 U | 11/1996 |
| JP | 8-512041 | 12/1996 |
| JP | 9059152 A | 3/1997 |
| JP | 11152224 A | 6/1999 |
| JP | 2000516633 A | 12/2000 |
| JP | 20086502 A | 7/2009 |
| KR | 2000-0029011 | 5/2000 |
| NO | 20032593 A | 8/2003 |
| PL | 178314 | 1/1995 |
| WO | WO8900570 A1 | 1/1989 |
| WO | WO8908127 A1 | 9/1989 |
| WO | WO9114677 A1 | 10/1991 |
| WO | WO9117164 A1 | 11/1991 |
| WO | WO9118887 A1 | 12/1991 |
| WO | WO9206979 A1 | 4/1992 |
| WO | 9212961 | 8/1992 |
| WO | WO9212969 A1 | 8/1992 |
| WO | WO9221328 A1 | 12/1992 |
| WO | WO9308190 A1 | 4/1993 |
| WO | WO9312090 A1 | 6/1993 |
| WO | 93015071 | 8/1993 |
| WO | WO9315055 A1 | 8/1993 |
| WO | WO9315056 A1 | 8/1993 |
| WO | WO9325517 A1 | 12/1993 |
| WO | 9402465 | 2/1994 |
| WO | WO9414795 A1 | 7/1994 |
| WO | WO9424130 A1 | 10/1994 |
| WO | WO9501338 A1 | 1/1995 |
| WO | WO9527714 A1 | 10/1995 |
| WO | WO9617830 A1 | 6/1996 |
| WO | WO9725030 A1 | 7/1997 |
| WO | WO9736905 A1 | 10/1997 |
| WO | WO9807400 A1 | 2/1998 |
| WO | WO9820858 A1 | 5/1998 |
| WO | WO9835683 A1 | 8/1998 |
| WO | WO9837080 A1 | 8/1998 |
| WO | WO9842707 A1 | 10/1998 |
| WO | WO9854188 A1 | 12/1998 |
| WO | WO9929299 A1 | 6/1999 |
| WO | WO9955705 A1 | 11/1999 |
| WO | WO9955706 A1 | 11/1999 |
| WO | WO9963940 A2 | 12/1999 |
| WO | 0012501 | 3/2000 |
| WO | WO0010999 A2 | 3/2000 |
| WO | WO0017200 A1 | 3/2000 |
| WO | WO0018388 A2 | 4/2000 |
| WO | WO0026217 A1 | 5/2000 |
| WO | WO0011000 A3 | 6/2000 |
| WO | WO0050011 A1 | 8/2000 |
| WO | 0051598 | 9/2000 |
| WO | WO0035428 A3 | 9/2000 |
| WO | WO0053182 A2 | 9/2000 |
| WO | WO0063211 A1 | 10/2000 |
| WO | WO0066123 A1 | 11/2000 |
| WO | WO0074654 A1 | 12/2000 |
| WO | WO0108686 A1 | 2/2001 |
| WO | WO0132165 A1 | 5/2001 |
| WO | 01046136 | 6/2001 |
| WO | WO0157025 A1 | 8/2001 |
| WO | WO0160358 A1 | 8/2001 |
| WO | WO0190076 A1 | 11/2001 |
| WO | WO0115678 A3 | 1/2002 |
| WO | WO0238155 A1 | 5/2002 |
| WO | WO0245693 A1 | 6/2002 |
| WO | WO02072072 A3 | 12/2002 |
| WO | 03039552 | 5/2003 |
| WO | WO03070279 A1 | 8/2003 |
| WO | 03097050 | 11/2003 |
| WO | 03105902 | 12/2003 |
| WO | WO03099334 A1 | 12/2003 |
| WO | 2004017974 | 3/2004 |
| WO | 2004019944 | 3/2004 |
| WO | 2004033430 | 4/2004 |
| WO | WO2004052345 A1 | 6/2004 |
| WO | WO2004066974 A1 | 8/2004 |
| WO | 2004080967 | 9/2004 |
| WO | 2004103407 | 12/2004 |
| WO | 2005011602 | 2/2005 |
| WO | WO2005013944 A1 | 2/2005 |
| WO | 2005026095 | 3/2005 |
| WO | 2005034871 | 4/2005 |
| WO | 2005041864 | 5/2005 |
| WO | WO2008006050 A2 | 1/2008 |

OTHER PUBLICATIONS

Hatzelmann et al, Anti-Inflammatory and Immunomodulatory Potential of the Novel PDE4 Inhibitor Roflumilast in Vitro, The Journal of Pharmacology and Experimental Therapeutics, 297(1), 267-279.*
Chiou et al, Review Article, Journal of Pharmaceutical Sciences, 1973, 60(9), 1281-1302.*
Hatzelmann et al, Anti-Inflammatory and Immunomodulatory Potential of the Novel PDE4 Inhibitor Roflumilast in Vitro, The Journal of Pharmacology and Experimental Therapeutics, 2000, 297(1), 267-279.*
Ammar H O Pharmazi (1997) vol. 52, pp. 627-631.
Anonym Inn Pharm Techn (2004) vol. 4, pp. 109-111 XP008050337.
Croda Japan KK Crodesta sucrose fatty acid ester, 2012.
Chiou W L J Pharm Sci (1971) vol. 60 pp. 1282-1302.
German E J Eye Lond 1999 Pub Med Result vol. 13 pp. 93-100.
Glenn M R Pharm Tech Europe (1994) pp. 24-35.
Hanifin J Journal of Investigative Dermatology (1996) vol. 107, pp. 51-56.
Kurashima T Jpn J Allergol (1991), pp. 160-163, vol. 40.
Lewis L., J. Microencapsulation vol. 15, No. 5 (1998), pp. 555-567 XP000771706.
Mueller R.H., Pharmazeutische Technologie Moderne Arzneiformen, (1997) pp. 80-91.
Odian G., Wiley Sons, (1991), pp. 19-23.
Pfizer Centre Source Dexamethasone USP Micronized (2010).
PVP disclosure—downloaded from the Internet (Jan. 21, 2008).
Reid P Current Opinion in Investigational Drugs (2002), vol. 3, No. 8, pp. 1165-1170 XP001119630.
Rolando M Survey of Ophthalmology (2001), vol. 45, pp. S203-S210.
Safety data sheet CRODESTA F10-HB03671 Sucrose Distearate Croda Europe Ltd (2005).
Safety data sheet CRODESTA F110 HB03722Sucrose Stearate and Sucrose Stearate Croda Europe Ltd (2005).
Safety data sheet CRODESTA F160 HB03750 Sucrose Stearate Croda Europe Ltd (2005).
Safety data sheet CRODESTA F20 HB03668 Sucrose Distearate Croda Europe Ltd (2005).
Safety data sheet CRODESTA F50 HB03669 Sucrose Distearate Croda Europe Ltd (2005).
Safety data sheet CRODESTA SL40 HB03791 Aqua and Sucrose Cocoate and Alcohol Croda Europe Ltd (2005).
Toshiro Murata Konando (1997) 5th edition pp. 112-114.

Response to Official Action and data filed Nov. 9, 2009. in corresponding European Patent Application No. 03704652.1-2123, 27 pages.

Baraniuk, James N. et al., "Inhibition of Phosphodiesterase 4 in Allergic Rhinitis", (Review of Schmidt et al., J Allergy Clin Immunol 108: 530-536 (2001)), Clinical Trials Report, pp. 191-193.

Barsig, Johannes et al., "The Novel Phosphodiesterase-4 Inhibitor Roflumilast Suppresses TNF-a Production and Efficiently Protects Mice Against Collagen-Induced Arthritis Alone and in Combination with Methotrexate", Arthritis and Rheumatic Diseases, 2001, vol. 44, No. 9, Suppl. S367, Abstract.

Barsig, J. et al., "The Novel Phosphodiesterase-4 Inhibitor Roflumilast Suppresses TNF-a Production and in Combination with Methotrexate Efficiently Protects Mice Against Collagen-induced Arthritis", Arthritis and Rheumatic Diseases, 2001, Poster Presentation.

Barsig, J. et al., "Protection by the Phosphodiesterase-4 Inhibitor Roflumilast of Mice Against Collagen-induced Arthritis", Poster Presentation, 2001.

Bethke, T. et al., "The New PDE4 Inhibitor Roftumilast Does Not Influence Cardiovascular Function", Am J Respir Crit Care Med, 2001, vol. 163, A431, Abstract.

Bethke, T. et al., "Roftumilast, a new, orally active, selective PDE4 inhibitor, does not interact with inhaled budesonide", Eur RespirJ, 2001, vol. 18, Suppl. 33, 156s, Abstract.

Bethke, T. et al., "Roftumilast, a New, Orally Active, Selective PDE4 Inhibitor, Does Not Interact with Inhaled Budesonide", Eur Respir J, 2001, Poster Presentation.

Bethke, T. et al., "Smoking has no effect on the pharmacokinetics of roftumilast, a new, orally active, selective PDE4 inhibitor", Eur RespirJ, 2001, vol. 18, Suppl. 33, 156s, Abstract.

Bundschuh, D.S. et al., "Antiinflammatory and Immunomodulatory Potential of Roftumilast, a Novel PDE4 Inhibitor", Am J Respir Crit Care Med, 2001, vol. 163, A431, Abstract.

Bundschuh, D.S. et al., "In vitro and in vivo anti-inflammatory activity of the novel PDE4 inhibitor roftumilast", Eur Respir J, 2001, vol. 18, Suppl. 33, 35s, Abstract.

Bundschuh. D.S. et al.. "In Vitro and in Vivo Anti-Inflammatory-Inflammatory Activity of the Novel PDE4 Inhibitor Roflumilast". Eur Respir J. 2001. Poster Presentation.

Bundschuh. Daniela S. et al.. "In Vivo Efficacy in Airway Disease Models of Roflumilast. a Novel Orally Active PDE4 Inhibitor", The Journal of Pharmacology and Experimental Therapeutics, 2001, vol. 297, No. 1, The American Society for Pharmacology and Experimental Therapeutics, pp. 280-290.

David, M. et al., "Influence of food intake on the pharmacokinetics of roflumilast, a new, orally active, selective PDE4 inhibitor", Eur RespirJ, 2001, vol. 18, Suppl. 33, 42s, Abstract.

David, M. et al., "Influence of Food Intake on the Pharmacokinetics of Roflumilast, a New, Orally Active, Selective PDE4 Inhibitor", Eur Respir J, 2001, Poster Presentation.

Hafner, Dietrich et al., "Additive Effects of Phosphodiesterase-4 Inhibition on Effects of rSP-C Surfactant", AmJ Respir Crit Care Med, 2000, vol. 161, pp. 1495-1500.

Washington Ocular drug delivery particulates (2000) pp. 265, 16 pages.

Hauns, B. et al., "Four-week treatment with the new PDE4 inhibitor roflumilast in patients with exercise-induced asthma: safety, efficacy and inhibition of TNF-a ex vivo", Eur Respir J, 2000, vol. 16, Suppl. 31, A3805, Abstract.

Hauns, B. et al., "Safety-related performance is not impaired by the new PDE-4 inhibitor Roftumilast", Eur Respir J, 2000, vol. 16, Suppl. 31, 277S, Abstract.

Herberg, KW. et al., "Treatment with the New PDE4 Inhibitor Roftumilast Does Not Impair Vigilance and Traffic Safety", Eur J Clin Pharmacol, 2000, vol. 56, No. 2, A29, Abstract.

Hoymann, H.G. et al., "Inhibition by Roftumilast of Airway Hyper-responsiveness to Acetylcholine 48H After Allergen Challenge in Rats", Am J Respir Crit Care Med, 2001, vol. 163, A431, Abstract.

Hoymann, H.G. et al., "Inhibition by Roftumilast of Airway Hyper-responsiveness to Acetylcholine 48 h after Allergen Challenge in Rats", Am J Respir Crit Care Med, 2001, Poster Presentation.

Hunnemeyer, A. et al., "Pharmacokinetics of Roftumilast and its Active Metabolite, Roflumilast-N-Oxide, Is Not Influenced by Smoking", Am J Respir Crit Care Med, 2002, vol. 165, A594, Abstract.

Hunnemeyer, A. et al., "Pharmacokinetics of Roftumilast and its Active Metabolite Roftumilast-N-Oxide Is Not Influenced by Smoking", Am J Respir Crit Care Med, 2002, Poster Presentation.

Izikki, Mohamed et al., "Effects of Roftumilast, a Phosphodiesterase-4 Inhibitor, on Hypoxia- and Monocrotaline-Induced Pulmonary Hypertension in Rats", The Journal of Pharmacology and Experimental Therapeutics, 2009, vol. 330, No. 1, pp. 54-62, The American Society for Pharmacology and Experimental Therapeutics.

Martin, Thomas J., "PDE4 inhibitors—A review of the recent patent literature", IDrugs, 2001, vol. 4, No. 3, pp. 312-338, PharmaPress Lld.

Nell, H. et al., "Acute Anti-Inflammatory Effect of the Novel Phosphodiesterase 4 Inhibitor Roftumilast on Allergen Challenge in Asthmatics After a Single Dose", Am J Respir Crit Care Med, 2000, vol. 161, No. 3, Part 2, A200, Abstract.

Poppe, H. et al., "Effects of a Selective PDE4-Inhibitor AWD 12-281 in Comparison With SB 207499 and Roflumilast on Tracheal Phenol Red Secretion in Mice and LPS-Induced Neutrophilia in BAL in Lewis Rats and Domestic Pigs", Am J Respir Crit Care Med, 2001, vol. 163, No. 5, A, Abstract.

Schmidt, Bernhard MW. et al., "The phosphodiesterase 4 inhibitor roftumilast is effective in the treatment of allergic rhinitis", J Allergy Clin Immunol, 2001, vol. 108, No. 4, pp. 530-536, Mosby, Inc.

Sorbera, L.A. et al., "Roftumilasl: Antialiergy/Antiasthmatic Treatment of COPD Phosphodiesterase 4 Inhibitor", Drugs of the Future, 2000, vol. 25, No. 12, pp. 1261-1264, Prous Science.

Timmer, W. et al., "Safety and Efficacy of the New PDE4 Inhibitor Roftumilast Administered to Patients with Exercise-Induced Asthma Over 4 Weeks", Am J Respir Crit Care Med, 2000, vol. 161, No. 3, Part 2, A505, Abstract.

Timmer, W. et al., "The Clinical Efficacy of the New PDE4 Inhibitor Roftumilast in Exercise-Induced Asthma is Accompanied by Suppression of LPS-Stimulated TNF-a Levels", Europ J Clin Pharm, 2000, vol. 56, No. 2, A29, Abstract.

Timmer, W. et al., "Treatment with Therapeutic Doses of the New PDE4 Inhibitor Roftumilast Does Not Influence Cardiovascular Function", Europ J Clin Pharm, 2000, vol. 56, No. 2, A29, Abstract.

Weimar, C. et al., "No interaction of roflumilast, a new, orally active, selective PDE4 inhibitor, with inhaled salbutamol", Eur RespirJ, 2001, vol. 18, Suppl. 33, 156s, Abstract.

Weimar, C. et al., "No Interaction of Roftumilast, a New, Orally Active, Selective PDE4 Inhibitor, with Inhaled Salbutamol", Eur Respir J, 2001, Poster Presentation.

Wollin, L. et al., "Inhibition by roftumilast of airway hyper-responsiveness to adenosine and pulmonary inflammation in allergen challenged Brown-Norway rats", Eur Respir J, 2001, vol. 18, Suppl. 33, 35s, Abstract.

Wollin, L. et al., "Inhibition by Roflumilast of Airway Hyper-responsiveness to Adenosine and Pulmonary Inflammation in Allergen-challenged Brown Norway Rats", Eur Respir J, 2001, Poster Presentation.

Wollin, L. et al., "Inhibition by Roflumilast of Airway Hyper-responsiveness to Adenosine and Pulmonary Neutrophil Accumulation 3H After Allergen Challenge in Rats", Am J Respir Crit Care Med, 2001, vol. 163, A432, Abstract.

Zech, K. et al., "High oral absolute bioavailability of roflumilast, a new, orally active, once daily PDE4 inhibitor", Eur Respir J, 2001, vol. 18, Suppl. 33, 20s, Abstract.

Pharmacy, 4th edition, p. 114-117, 2012.

Keipert et al., Pharmazie (1986) vol. 41, pp. 400-404.

Meyer, H., "Charackterisierung und Beeinflussung der Losungseigenschaften von 6-Bromcip", Dissertation 1995, p. 154-189, (1995).

Bauer, et al., "Lehrbuch der Pharmazeutischen Technologie", p. 56, (2003).

Yliruusi, J. K., et al., "A new Method to evaluate the elastic behavior of tablets during compression", Drug: Oev. Ind. Pharm., vol. 23, No. 1, p. 63-68, (1997), 1 pg.

"Glossary", Ph Eur Monogra)2h, vol. 1502, p. 1-2, (2005).
Tros De Ilarduya M C Drug Development and Industrial Pharmacy (1998) vol. 24, pp. 295-300.
Zelko, R., et al., "Effects of storage conditions on the free volume of polyvinylpyrrolidone: comparison of positron lifetime data with tensile strength of tablet", Pharm. Res., vol. 17, No. 8, p. 1030-1032, (2000), 2 pg.
Buehler, V., "Kollidon: Polyvinylpyrrolidone for the pharmaceutical industry", 6th Ed., BASF, p. 1-287, (1995).
Tros de Ilarduya et al., "Solubilization and Interaction of Sulindac with Polyvinylpyrrolidone K30 in the Solid State and in Aqueous Solution", Drug Development and Industrial Pharmacy, 24(3), 295-300 (1998).
Ammar et al., "Improvement of the biological performance of oral anticoagulant drugs", Pharmazie 52 pp. 627-631 (1997).
Academic book Applied Pharmacy Farmacja Stosowana Fiebig Janicki p. 267-268 2001 (English translation).
Antoni et al., "Synthesis of [18F] Labelled Roflumilast Using Difluoro [18F] Bromomethane as Alkylating Agent," Synthesis and Applications of Isotopically Labeled Compounds, vol. 7, pp. 375-376 (2000).
Assmann S F Lancet 2000 vol. 355 p. 1064-1069.
BEERS_M Merck_Manual_of_Diagnosis_and_Therapy 17th_Edition 1999 p_568-569 XP002300786.
*Brusasco* v *Thorax* 2003 vol. 58, p. 399-404.
Calverly P M a Lancet 2009 vol. 374 p. 685-694.
Calverly P M Am J Respir Crit Care Med 2007 vol. 176 p. 154-161.
Calverly P M Eur Respir J 2003 vol. 22 p. 912-919.
Calverly P M Lancet 2003 vol. 362 p. 1053-1061.
Calverly P M N Engl J Med 2007 vol. 356 p. 775-789.
Calverly P M Respir Res 2008 vol. 9 p. 73.
Calverly, P., Lancet 2003, vol. 361, pp. 449-456.
Casas J P J Intern Med 2008 vol. 264 p. 295-314.
COCCI_F Int_J_Biochem_Cell_Biol 2002 Vol_36 No_6 pp_594-604.
Cook, D.C., et al., "Process Development o the PDE IV Inhibitor 3-(Cyclopentyloxy)- N-(3,5- dichloropyrid-4-yl)-4-methoxybenzamide," *Organic Process Research & Development*, vol. 2, pp. 157-168, 1998.
Definition of solution colloidal from Hawleys Chemical Condensed Dictionary 14th edition 2002.
Donaldson G C Thorax 2002 vol. 57 p. 847-852.
Drugs_in_R_and_D 2004 Vol_5 No_3 p_176-181 XP008036613.
Exhibit B-5 Handbook of Pharmaceutical Excipients 2nd Ed 1994.
Exhibit B-6 Release controlled Oral Preparation, 2013.
Fabbri L M Lancet 2009 vol. 374 p. 695-703.
Fialkov Y., Chemical Abstracts 1983 Vol_98 No_23 p_603.
Fox J Am J Resp Crit Care Med 2003 vol. 167 p. A91.
GRISWOLD_D Journal_of_Pharmacology_and_Experimental_Therapeuctics 1998 Vol_287 No_2 p_705-711.
Grootendorst D C Thorax 2007 vol. 62 p. 1081-1087.
Hahn H., Chemical Abstracts 1963 Vol_58 No_9.
Hermann R J Clin Pharmacol 2007 vol. 47 p. 1005-1013.
Hilden L R J of Pharma Sciences 2004 p. 3-12 vol. 93.
Kast Pharmaceutics 1998, pp. 361-366 (Engilsh translation).
Kazumasa S., Chemical Abstracts 1988 Vol_108 No_15 Abstract No_131583p.
Kessler R Chest 2006 vol. 130 p. 133-142.
Kumar Rakesh KJ Pharmacol Exp Ther 2003 vol. 307 p. 349-355.
Lahu G J Clin Pharm 2010.
Lanes S F Am J Respir Crit Care Med 2008 vol. 178 p. 543-544.
MACINTYRE_N_R Pharmacotherapy 2004 Vol_24 No_5 p_33S-43S XP008036609.
Mahler D A Chest 1984 vol. 85 p. 751-758.
Norman P. Expert Opinion Therapeutic Patents 1999 pp. 1101-1118 vol. 9 No. 8.
Pruniaux M Am J Resp Crit Care Med 2003 vol. 167 p. A874.
Rabe K F A J Respir Crit Care Med 2007 vol. 176 p. 532-555.
Rabe K F Expert Reviews Resp Med 2010 vol. 4 p. 543-555.
Rabe K F Lancet 2005 vol. 366 p. 563-571.
Rabe Lancet 2005 vol. 366 p. 1846-1847.
Rabin R Ann Med 2001 vol. 33 p. 337-343.
REID_P_T Current_Pharmaceutical_Design 2003 Vol_9 p_25-38 XP008036607.
RENNARD_S Respiratory Research 2011 vol. 18 p. 12.
Sin D D Thorax 2006 vol. 61 p. 1-3.
Snoeck-Stroband J B Eur Respir J 2008 vol. 31 p. 70-77.
Soler-Cataluna JJ Thorax 2005 vol. 60 p. 925-931.
Solutol HS Technical Information Jul. 2003.
Spencer S Am J Respir Crit Care Med 2001 vol. 163 p. 122-128.
Spina D Br J Pharmacol 2008 vol. 155 p. 308-315.
Stebbins K Am J Resp Crit Care Med 2003 vol. 167 p. A486.
Stockley R A Thorax 2006 vol. 61 p. 122-128.
Strickley R G Pharmaceutical Research 2004 vol. 21 2 p. 201-230.
Tashkin D P N Engl J Med 2008 vol. 359 p. 1543-1554.
THURLBECK_W_M American_Review_Respiratory_Disease 1967 Vol_95 No_5 p_752-764.
Von Richter O Clin Pharmacokin 2007 vol. 46 p. 613-622.
YAGUPOLSKII_L_M Chemical Abstracts 1961 Vol_55 No_18.
Bethke, et al., "Smoking Has No Effect on the Pharmacokinetics of Roflumilast—a New, Orally Active, Selective PDE4 Inhibitor," Eur Respir J., Poster Presentation, 2013.
Non-Final Rejection mailed Feb. 29, 2012, which issued in corresponding U.S. Appl. No. 12/876,996.
Sucker, H., Pharmazeutische Technologie: Beschrelbung der Arznelformen Speziele Entwicklung der Dermatika, p. 629-636 and p. 650-665 (1978).
Response to EPO Communication Pursuant Article 94-3 (2009).
EPO Office Action Dated Nov. 19, 2010 in corresponding EP case citing EP1161950A1.
CN Office Action dated Mar. 29, 2009.
EC Office Action dated Jul. 31, 2008.
JP Office Action dated Sep. 14, 2007.
KR Office Action dated Oct. 7, 2010.
Office Action PH Jun. 16, 2009.
Office Action dated May 19, 2010 in U.S. Appl. No. 11/342,621.
Office Action dated Aug. 9, 2010 in U.S. Appl. No. 11/342,621.
Office Action dated Jan. 11, 2006 in U.S. Patent No. 7,175,854.
Office Action dated Apr. 20, 2010 in U.S. Appl. No. 12/149,250.
Office Action dated Oct. 22, 2010 in U.S. Appl. No. 12/149,250.
Office Action dated Oct. 9, 2007 in U.S. Appl. No. 10/515,698.
Office Action dated Jan. 23, 2008 in U.S. Appl. No. 10/515,698.
Office Action dated Jul. 24, 2008 in U.S. Appl. No. 10/515,698.
Office Action dated Mar. 13, 2009 in U.S. Appl. No. 10/515,896.
Office Action dated Mar. 26, 2010 in U.S. Appl. No. 10/515,896.
Office Action dated Dec. 20, 2007 in U.S. Appl. No. 11/885,837.
Office Action dated Oct. 14, 2010 in U.S. Appl. No. 11/885,837.
Kollidone Handbook 4th ed., BASF, 1998.
Opposition filed in the name of Hexal AG against EP1478399 of Nycomed GmbH, filed Feb. 20, 2003, granted Mar. 21, 2012.

* cited by examiner

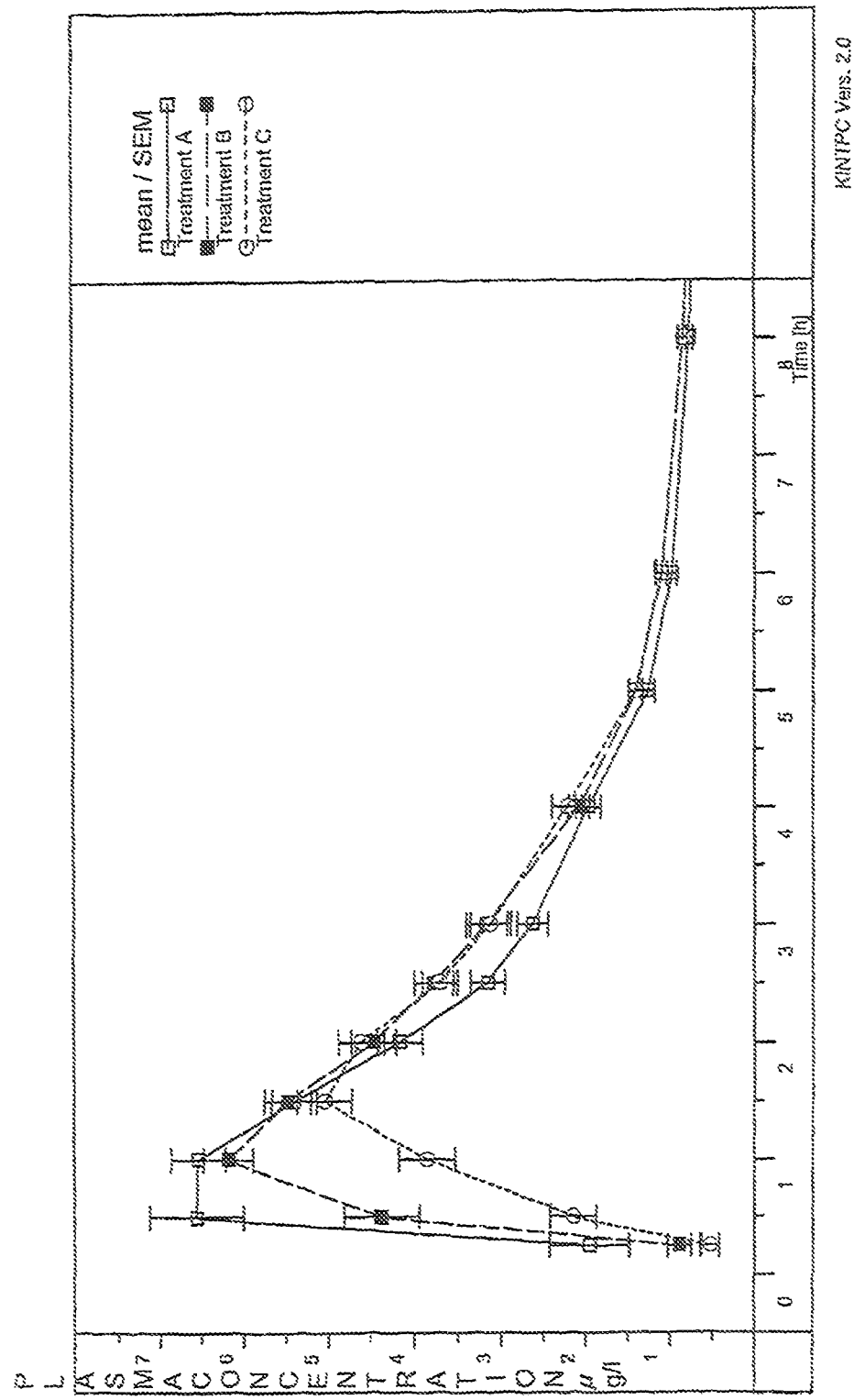

ORAL DOSAGE FORM CONTAINING A PDE 4 INHIBITOR AS AN ACTIVE INGREDIENT AND POLYVINYLPYRROLIDONE AS EXCIPIENT

The present invention is a continuation of U.S. patent application Ser. No. 10/505,138, filed Aug. 19, 2004, now U.S. Pat. No. 7,951,397, which is a national stage entry of PCT/EP03/01650, filed Feb. 19, 2003, which claims priority to European Patent Office 02004811.3, filed Feb. 20, 2002, and further claims priority to Germany 10207160.8, filed Feb. 20, 2002. The present invention relates to the field of pharmaceutical technology and describes a dosage form for oral administration of a PDE 4 inhibitor as active ingredient in tablet or pellet form for treating diseases such as asthma or airway obstructions. The invention additionally relates to processes for producing the dosage form.

TECHNICAL FIELD

The present invention relates to the field of pharmaceutical technology and describes a dosage form for oral administration of a PDE 4 inhibitor as active ingredient in tablet or pellet form for treating diseases such as asthma or airway obstructions. The invention additionally relates to processes for producing the dosage form.

PRIOR ART

Cyclic nucleotide phosphodiesterase (PDE) inhibitors (specifically of type 4) are currently of special interest as a new generation of active ingredients for treating inflammatory disorders, especially inflammations of the airways such as asthma or airway obstructions (such as, for example, COPD=chronic obstructive pulmonary disease). A number of PDE 4 inhibitors is currently undergoing advanced clinical testing.

In WO00/50011 and WO01/32165, which relate to dosage forms with controlled or sustained delivery of a PDE 4 inhibitor, it is pointed out that unwanted CNS side effects may become manifest on delivery of certain PDE 4 inhibitors such as Ariflo®(INN: cilomilast) in higher dosages. WO00/50011 and WO01/32165 see this as being a particular risk with immediate release dosage forms of the active ingredient and therefore propose administering the PDE 4 inhibitor Ariflo® (INN: cilomilast) in dosage forms with controlled or sustained release.

U.S. Pat. No. 5,286,494 proposes a dosage form with controlled or sustained release for the PDE 4 inhibitor Rolipram whose solubility is slight. However, production of dosage forms with controlled or sustained release of slightly soluble active ingredients may be technically complicated, reference being made thereto for example in U.S. Pat. No. 5,286,494.

The solubility of active ingredients of the PDE 4 inhibitor class in water and aqueous systems may, depending on the chemical structure, be low. Thus, the solubility in water found for the PDE 4 inhibitor N-(3,5-dichloropyrid-4-yl)-3-cyclopropylmethoxy-4-difluoromethoxybenzamide (INN: roflumilast), which is described in WO95/01338, is only 0.53 mg/l at 21° C. The bioavailability of a medicinal substance depends essentially on the release of the medicinal substance from the pharmaceutical form. Faster release and dissolution of the medicinal substance from the formulation means faster absorption thereof. With medicinal substances which are slightly soluble in water, therefore, the bioavailability is frequently limited by the solubility or rate of dissolution. This makes it very difficult to produce suitable dosage forms.

DESCRIPTION OF THE INVENTION

It is an object of the present invention to provide a dosage form for oral administration of PDE 4 inhibitors whose solubility is slight, which form can be produced without great technical complexity, which takes account of the low solubility of the PDE 4 inhibitor whose solubility is slight, and which results in rapid, acceptable bioavailability of the PDE 4 inhibitor whose solubility is slight, so as to attain serum levels which are required in order to obtain the desired pharmacological effect quickly without side effects becoming manifest.

It has now been found, surprisingly, that this object can be achieved by a dosage form for oral administration of a PDE 4 inhibitor whose solubility is slight, employing polyvinylpyrrolidone (PVP) as binder for the dosage form. Compared with dosage forms in which no PVP is employed as binder, the dosage form of the invention shows distinctly improved pharmacokinetic properties. Thus, in particular in relation to the bioavailability of the PDE 4 inhibitor whose solubility is slight, a faster absorption and thus faster onset of the pharmacological effect is observed with the dosage forms of the invention compared with dosage forms without PVP. The oral dosage form of the invention is preferably a solid dosage form in tablet or pellet form. It is preferably a solid oral dosage form with immediate release of the active ingredient (immediate release solid oral dosage form).

The invention therefore relates to a dosage form in tablet or pellet form for oral administration of a PDE 4 inhibitor whose solubility is slight, comprising the PDE 4 inhibitor whose solubility is slight together with polyvinylpyrrolidone as binder, and one or more other suitable pharmaceutical excipients.

The PDE 4 inhibitor whose solubility is slight is preferably according to the invention a compound from the group of compounds of the formula I

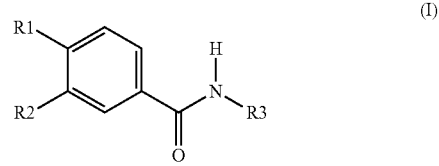

in which either

R1 is 3-7C cycloalkoxy, 3-7C cycloalkylmethoxy or benzyloxy and

R2 is 1-4C alkoxy which is completely or partly substituted by fluorine.

or

R1 is 1-4C alkoxy which is completely or partly substituted by fluorine and

R2 is 3-7C cycloalkylmethoxy or benzyloxy, and

R3 is phenyl, pyridyl, phenyl substituted by R31, R32 and R33, or pyridyl substituted by R34, R35, R36 and R37, where R31 is hydroxyl, halogen, cyano, carboxyl, trifluoromethyl, 1-4C alkyl, 1-4C alkoxy, 1-4C alkoxy-carbonyl, 1-4C alkylcarbonyl, 1-4C alkylcarbonyloxy, amino, mono- or di-4C alkylamino or 1-4C alkylcarbonylamino, R32 is hydrogen, hydroxyl, halogen, amino, trifluoromethyl, 1-4C alkyl or 1-4C alkoxy,
R33 is hydrogen, halogen, 1-4C alkyl or 1-4C alkoxy,
R34 is hydroxyl, halogen, cyano, carboxyl, 1-4C alkyl, 1-4C alkoxy, 1-4C alkoxycarbonyl or amino,
R35 is hydrogen, halogen, amino or 1-4C alkyl,
R36 is hydrogen or halogen and
R37 is hydrogen or halogen,
the salts of these compounds and the N-oxides of the pyridines and the salts thereof.

3-7C Cycloalkoxy is, for example, cyclopropyloxy, cyclobutyloxy, cyclopentyloxy, cyclohexyloxy and cycloheptyloxy, of which cyclopropyloxy, cyclobutyloxy and cyclopentyloxy are preferred.

3-7C Cycloalkylmethoxy is, for example, cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Examples which may be mentioned of 1-4C alkoxy which is completely or partly substituted by fluorine are 1,2,2-trifluoroethoxy, 2,2,3,3,3-pentafluoropropoxy, perfluoroethoxy and, in particular, 1,1,2,2-tetra-fluoroethoxy, trifluoromethoxy, 2,2,2-trifluoroethoxy and difluoromethoxy radicals.

Halogen for the purposes of the present invention is bromine, chlorine and fluorine.

1-4C Alkyl represents straight-chain or branched alkyl radicals having 1 to 4 carbon atoms. Examples which may be mentioned are butyl, isobutyl, sec-butyl, tert-butyl, propyl, isopropyl, ethyl and methyl radicals.

1-4C Alkoxy is a radical which, besides the oxygen atom, contains one of the aforementioned 1-4C alkyl radicals. Examples which may be mentioned are the methoxy and ethoxy radicals.

1-4C Alkoxycarbonyl is a carbonyl group to which one of the aforementioned 1-4C alkoxy radicals is bonded. Examples which may be mentioned are the methoxycarbonyl ($CH_3O-CO-$) and ethoxycarbonyl ($CH_3CH_2O-CO-$) radicals.

1-4C Alkylcarbonyl is a carbonyl group to which one of the aforementioned 1-4C alkyl radicals is bonded. An example which may be mentioned is the acetyl radical ($CH_3CO-$).

1-4C Alkylcarbonyloxy radicals, comprise besides the oxygen atom one of the aforementioned 1-4C alkylcarbonyl radicals. An example which may be mentioned is the acetoxy radical ($CH_3CO-O-$).

Examples of mono- or di-1-4C alkylamino radicals which may be mentioned are the methylamino, dimethylamino and diethylamino radicals.

An example of a 1-4C alkylcarbonylamino radical which may be mentioned is the acetylamino radical ($-NH-CO-CH_3$).

Examples of phenyl radicals substituted by R31, R32 and R33 which may be mentioned are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxy-phenyl, 2,4-dimethoxyphenyl, 2,6-dimethoxyphenyl, 2-dimethylaminophenyl, 2-methylphenyl, 2-chloro-6-methylphenyl, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Examples of pyridyl radicals substituted by R34, R35, R36 and R37 which may be mentioned are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trifluoropyrid-4-yl and 2,3,5-trifluoropyrid-4-yl.

Salts suitable for compounds of the formula I—depending on the substitution—are all acid addition salts but, in particular, all salts with bases. Particular mention may be made of the pharmacologically acceptable salts of the inorganic and organic acids and bases normally used in pharmaceutical technology. Pharmacologically unacceptable salts which, for example, may be the initial products of the process for preparing the compounds of the invention on the industrial scale are converted into pharmacologically acceptable salts by processes known to the skilled worker. Those suitable on the one hand are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid, or 3-hydroxy-2-naphthoic acid, the acids being employed to prepare the salts in the equimolar ratio of amounts, or one differing therefrom—depending on whether the acid is monobasic or polybasic and depending on which salt is desired.

On the other hand, salts with bases are also particularly suitable. Examples of basic salts which may be mentioned are lithium, sodium, potassium, calcium, aluminum, magnesium, titanium, ammonium, meglumine or guanidinium salts, once again the bases being employed to prepare the salts in the equimolar ratio of amounts or one differing therefrom.

Compounds of the formula I to be emphasized are those in which either
R1 is 3-5C cycloalkoxy, 3-5C cycloalkylmethoxy or benzyloxy and
R2 is 1-4C alkoxy which is completely or partly substituted by fluorine,
or
R1 is 1-4C alkoxy which is completely or partly substituted by fluorine and
R2 is 3-5C cycloalkylmethoxy or benzyloxy,
and
R3 is phenyl, pyridyl, phenyl substituted by R31, R32 and R33, or pyridyl substituted by R34, R35, R36 and R37, where
R31 is halogen, cyano, carboxyl, 1-4C alkyl, 1-4C alkoxy or 1-4C alkoxycarbonyl,
R32 is hydrogen, halogen, 1-4C alkyl or 1-4C alkoxy,
R33 is hydrogen, halogen, 1-4C alkyl or 1-4C alkoxy,
R34 is halogen or 1-4C alkyl,
R35 is hydrogen or halogen,
R36 is hydrogen or halogen and
R37 is hydrogen or halogen, the salts of these compounds, and the N-oxides of the pyridines and salts thereof.

Compounds of the formula I to be particularly emphasized are those in which either R1 is 3-5C cycloalkoxy, 3-5C cycloalkylmethoxy or benzyloxy and
R2 is 1-4C alkoxy which is completely or partly substituted by fluorine,
or
R1 is 1-4C alkoxy which is completely or partly substituted by fluorine and
R2 is 3-5C cycloalkylmethoxy or benzyloxy and
R3 is 2-bromophenyl, 2,6-dichloro-4-ethoxycarbonylphenyl, 2,6-dimethoxyphenyl, 4-cyano-2-fluoro-phenyl), 2,4,6-trifluorophenyl, 2-chloro-6-methylphenyl, 2,6-dimethylphenyl, 2,6-difluorophenyl, 2,6-dichlorophenyl, 3,5-dichloropyrid-4-yl, 3-methylpyrid-2-yl, 2-chloropyrid-3-yl, 3,5-dibromopyrid-2-yl, 2,3,516-tetrafluoropyrid-4-yl, 3-chloro-2,5,5-trifluoropyrid-4-yl, 3,5-dichloro-2,6-difluoropyrid-4-yl or 2,6-dichloropyrid-3-yl,
the salts of these compounds, and the N-oxides of the pyridines and salts thereof.

Preferred compounds of the formula I are those in which
R1 is difluoromethoxy,
R2 is cyclopropylmethoxy and
R3 is 2-bromophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2,6-difluoro-phenyl, 2,6-dichlorophenyl, 3,5-dichloropyrid-4-yl, 3-methylpyrid-2-yl, 2-chloropyrid-3-yl, 3,5-dibromopyrid-2-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
the salts of these compounds, and the N-oxides of the pyridines and salts thereof.

A particularly preferred compound of the formula I is the one in which
R1 is difluoromethoxy,
R2 is cyclopropylmethoxy and
R3 is 3,5-dichloropyrid-4-yl,
the salts of these compounds, and the N-oxide of the pyridine and salts thereof.

This compound has the chemical name N-(3,5-dichloropyrid-4-yl)-3-cyclopropylmethoxy-4-difluoromethoxybenzamide (INN: roflumilast).

The PDE 4 inhibitor whose solubility is slight is preferably a PDE 4 inhibitor with a solubility in water of less than or equal to 100 milligram/liter, particularly preferably with a solubility in water of less than or equal to 1 milligram/liter, at a temperature of 15 to 25° C., in particular at 21° C. This compound is particularly preferably one of the formula I.

The abovementioned compounds of the formula I and the use of these compounds as phosphodiesterase (PDE) 4 inhibitors are described in the international patent application WO95/01338.

Further suitable pharmaceutical excipients which may be used in the dosage form of the invention are pharmaceutical excipients such as fillers, additional binders, tablet disintegrants or else lubricants and release agents. Other suitable excipients which may be present in the dosage form of the invention are, for example, flavoring substances (such as flavors and sweeteners), buffer substances, preservatives, coloring substances (such as iron oxid yellow or red) or else emulsifiers. Flavors are usually added in a proportion of from 0.05 to 1% by weight. Other flavoring substances by way of example are acids such as citric acid, sweeteners such as saccharin, aspartame, cyclamate sodium or maltol, which are added according to the desired result.

The polyvinylpyrrolidone (PVP) employed according to the invention is, in particular, a water-soluble PVP with an average molecular weight above 2 000; preferably above 20 000. Examples which may be mentioned are Kollidon 12 PF (molecular weight 2 000-3 000), Kollidon 17 PF (molecular weight 7 000-11 000), Kollidon 25 (molecular weight 28 000-34 000), Kollidon 30 (molecular weight 44 000-54 000), Kollidon 90 F (molecular weight 1 000 000-1 500 000). PVP of higher molecular weight such as, for example, Kollidon 25, Kollidon 30 and Kollidon 90 F may be mentioned as preferred.

It is possible if desired to employ in addition to PVP other binders such as polyvinyl acetate (e.g. Kollidon® VA 64), gelatin, corn starch mucilage, preswollen starches (Starch 1500), hydroxypropyl-methylcellulose (HPMC) or hydroxypropylcellulose (L-HPC).

Fillers suitable according to the invention are fillers such as calcium carbonate (e.g. MagGran® CC or Destab®95) and sodium carbonate, sugar alcohols such as mannitol (e.g. Perlitol® or Parteck® M), sorbitol (e.g. Karion®), xylitol or maltitol, starches such as corn starch, potato starch and wheat starch, microcrystalline cellulose, saccharides such as glucose, lactose (e.g. lactose monohydrate), levulose, sucrose and dextrose. It is also possible if desired to use mixtures thereof. Corn starch, microcrystalline cellulose and lactose may be mentioned as preferred.

Examples of suitable lubricants and release agents which may be mentioned are sodium stearyl fumarate, magnesium stearate, calcium, stearate, stearic acid, talc and colloidal anhydrous silica (Aerosil).

Disintegrants suitable according to the invention are, in particular, insoluble polyvinylpyrrolidone (insoluble PVP, crospovidone), carboxymethylstarch sodium [=sodium starch glycolate], sodium carboxymethylcellulose, alginic acid, and starches able to carry out the function of a disintegrant (e.g. Starch 1500).

The proportion (in percent by weight based on the finished dosage form) of PDE 4 inhibitor in the dosage form of the invention is usually, depending on the nature of the PDE 4 inhibitor, from 0.01 to 50% by weight. The proportion of PDE 4 inhibitor is preferably up to 20% by weight.

The proportion (in percent by weight based on the finished dosage form) of binder (PVP and, where appropriate, other binders) may preferably be according to the invention from 0.5 to 20% by weight. The proportion of PVP is preferably from 1 to 5% by weight, particularly preferably 2 to 3% by weight.

The proportion (in percent by weight based on the finished dosage form) of filler in the tablet of the invention is advantageously from 40 to 99% by weight, the proportion of filler is preferably from 60 to 97% by weight.

The proportion (in percent by weight based on the finished dosage form) of disintegrant in the rapidly disintegrating tablet can usually be up to 35% by weight. The proportion of disintegrant is preferably from 2 to 20% by weight. The proportion of disintegrant is particularly preferably from 5 to 10% by weight.

The proportion (in percent by weight based on the finished dosage form) of lubricant or release agent in the rapidly disintegrating tablet is usually from 0.1 to 5% by weight. The proportion of lubricant or release agent is preferably from 0.3 to 3% by weight. The proportion of lubricant or release agent is particularly preferably from 0.5 to 2% by weight.

In a preferred embodiment of the invention, the dosage form is a tablet. It is preferred for the tablet, besides the PDE 4 inhibitor whose solubility is slight and PVP, to comprise as further pharmaceutical excipients at least one filler and at least one lubricant or release agent.

The pharmaceutical preparation of the invention can be produced by processes known to the skilled worker for producing tablets and pellets.

In one embodiment of the invention, the pharmaceutical form of the invention is produced by producing a solid solution of the PDE 4 inhibitor whose solubility is slight in the binder PVP as carrier. This can take place for example by the solvent method in which PVP, the PDE 4 inhibitor and, where appropriate, other pharmaceutical excipients are dissolved in a suitable solvent, and the solvent is subsequently removed again by spray drying, normal drying, vacuum drying or freeze-drying. It has been found, surprisingly, that production of the solid solution is also possible by the mixing method in which a PDE 4 inhibitor whose solubility is slight and, where appropriate, other pharmaceutical excipients are vigorously mixed together with PVP.

The invention also relates further to a solid solution of a PDE 4 inhibitor whose solubility is slight in the binder PVP as carrier. A solid solution of the PDE 4 inhibitor in the binder PVP as carrier means according to the invention a solid solution with amorphous structure in which the PDE 4 inhibitor is in the form of a molecular dispersion in the carrier material.

In the event of further processing of a solid solution to tablets or pellets, the solid solution may be processed as active ingredient component together with the filler, binder, disintegrant and lubricant components by production processes familiar to the skilled worker to give the oral dosage forms of the invention.

The invention therefore also relates to a process for producing a dosage form in tablet or pellet form for oral administration of a PDE 4 inhibitor, comprising the steps: (a) production of an active ingredient preparation in the form of a solid solution in PVP of the PDE 4 inhibitor whose solubility is slight, (b) production of a mixture of an active ingredient preparation and pharmaceutical excipients and (c) granulation of the mixture obtained in (b) with an aqueous solution of PVP.

In the case of dosage forms of the invention in the form of tablets, the granules obtained in (c) can, after drying and mixing with lubricants or release agents, be compressed in a tablet press. In the case of dosage forms of the invention in the form of pellets, the wet granules obtained in (c) can be processed by the extruder/spheroidizer process to suitable pellets. Alternatively, dispersions/suspensions of an active ingredient preparation can be applied in the form of a solid solution in PVP of the PDE 4 inhibitor whose solubility is slight in a suitable solvent to pellet-like carriers (e.g. nonpareils or HPMC-containing pellets).

In another preferred embodiment of the invention, the dosage form of the invention is produced by granulating a mixture of active ingredient and pharmaceutical excipients with an aqueous PVP solution, drying the granules and, if desired, admixing other pharmaceutical excipients. Wet preparations obtained after granulation can then be further processed to pellets and can subsequently be packed into capsules. Dried granules can—if desired after admixture of other pharmaceutical excipients—after mixing with a release agent be compressed in a tablet press. The granulation preferably takes place in a fluidized bed granulated under suitable conditions. It is moreover possible if desired for the active ingredient to be admixed to the other pharmaceutical excipients in the form of a trituration with a pharmaceutical excipient (especially a filler). This is particularly preferred when the active ingredient content in the dosage form is less than 5% by weight. Such a trituration can normally be obtained by grinding the active ingredient with a pharmaceutical excipient (especially a filler).

The invention therefore also relates to a process for producing a dosage form in tablet or pellet form for oral administration of a PDE 4 inhibitor comprising the steps:
(a) production of a mixture of active ingredient and pharmaceutical excipients and
(b) granulation of the mixture obtained in (a) with an aqueous solution of PVP.

The dosage form of the invention is particularly preferably produced by granulation of a mixture of
(a) PDE 4 inhibitor whose solubility is slight, or a trituration of the PDE 4 inhibitor whose solubility is slight with corn starch,
(b) corn starch and
(c) lactose monohydrate
with an aqueous PVP solution, drying of the granules, mixing of the granules with a release agent and compression in a tablet press. The PDE 4 inhibitor whose solubility is slight is in this case particularly preferably roflumilast, the salts thereof, the N-oxide of the pyridine and salts thereof.

Alternatively, the dosage form of the invention is particularly preferably produced by granulation of a mixture of
(a) PDE 4 inhibitor whose solubility is slight, or a trituration of the PDE 4 inhibitor whose solubility is slight with corn starch,
(b) corn starch,
(c) microcrystalline cellulose and
(d) sodium carboxymethylstarch
with an aqueous PVP solution, drying of the granules, mixing of the granules with a release agent and compression in a tablet press. The PDE 4 inhibitor whose solubility is slight is in this case particularly preferably roflumilast, the salts thereof, the N-oxide of the pyridine and salts thereof.

In a further preferred embodiment of the invention, the dosage form of the invention is produced by granulation of a mixture of pharmaceutical excipients with a suspension of the active ingredient in an aqueous PVP solution, drying of the granules and, if desired, admixture of further pharmaceutical excipients. The preparations obtained in this way can then, after mixing with a release agent, be compressed in a tablet press. The granulation preferably takes place in a fluidized bed granulator under suitable conditions.

The invention therefore also relates to a process for producing a dosage form in tablet or pellet form for oral administration of a PDE 4 inhibitor comprising the steps:
(a) production of a mixture of pharmaceutical excipients and
(b) granulation of the mixture obtained in (a) with a suspension of the active ingredient in an aqueous solution of PVP.

The dosage form of the invention is particularly preferably produced by granulation of a mixture of corn starch and lactose monohydrate with a suspension of the PDE 4 inhibitor whose solubility is slight in an aqueous solution of PVP, drying of the granules, mixing of the granules with a release agent and compression in a tablet press.

It has surprisingly been found that dosage forms of the invention produced employing physical mixtures or triturations of the PDE 4 inhibitor whose solubility is slight with a filler (e.g. by grinding, vigorous mixing or extrusion) and subsequent granulation with aqueous PVP solutions, or produced employing granulation suspensions of PDE 4 inhibitors in aqueous PVP solutions, have similar advantageous properties in relation to the bioavailability of the PDE 4 inhibitor whose, solubility is slight as do dosage forms produced by first producing solid solutions of PVP and PDE 4 inhibitor. This suggests that in the production of the dosage forms of the invention based on physical mixtures or triturations of the PDE 4 inhibitor whose solubility is slight with a filler, which are subsequently granulated with aqueous PVP solutions, or in whose preparation granulation suspensions of PDE 4 inhibitors in aqueous PVP solutions are employed, there are, surprisingly, interactions between PVP and PDE 4 inhibitor whose solubility is slight, like those occurring in the solid solution of PVP and PDE 4 inhibitor. In the production of the dosage forms of the invention it is therefore also possible to dispense with the more technically elaborate variant of production of a solid solution by the solvent method.

DESCRIPTION OF THE FIGURE

FIG. 1 shows the time course of the average serum concentration of roflumilast after oral administration of 0.5 mg (2 tablets each containing 0.25 mg) of roflumilast from dosage forms of the invention compared with a dosage form containing no PVP.

The production of tablets and preparations of the invention is described by way of example below. The following examples explain the invention in more detail without restricting it.

EXAMPLES

Production of Tablets of the Invention

Example A

| | Weight based on a tablet containing 0.1 mg of roflumilast | |
|---|---|---|
| 1. | Roflumilast (micronized) | 0.100 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
| | Total | 65.100 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.1 mg.

Example B

| | Weight based on a tablet containing 0.125 mg of roflumilast | |
|---|---|---|
| 1. | Roflumilast | 0.125 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
| | Total | 65.125 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.125 mg.

Example C

| | Weight based on a tablet containing 0.25 mg of roflumilast | |
|---|---|---|
| 1. | Roflumilast | 0.250 mg |
| 2. | Microcrystalline cellulose | 33.900 mg |
| 3. | Corn starch | 2.500 mg |
| 4. | Polyvidone K90 | 2.250 mg |
| 5. | Sodium carboxymethylstarch (type A) | 20.000 mg |
| 6. | Magnesium stearate (vegetable) | 0.600 mg |
| | Total | 59.500 mg |

Production: (1) is mixed with part of (3), and a trituration is produced in a planetary mill. The trituration is put together with (2), (5) and the remaining amount of (3) in the product container of a fluidized bed granulation system, and a 5% granulation solution of (4) in purified water is sprayed on and dried under suitable conditions. (6) is added to the granules, and the mixture obtained after mixing is compressed in a tablet press to tablets having an average weight of 59.5 mg.

Example D

| | Weight based on a tablet containing 0.25 mg of roflumilast | |
|---|---|---|
| 1. | Roflumilast | 0.250 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
| | Total | 65.250 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.25 mg.

Example E

| | Weight based on a tablet containing 0.5 mg of roflumilast | |
|---|---|---|
| 1. | Roflumilast | 0.500 mg |
| 2. | Lactose monohydrate | 49.660 mg |
| 3. | Corn starch | 13.390 mg |
| 4. | Polyvidone K90 | 1.300 mg |
| 5. | Magnesium stearate (vegetable) | 0.650 mg |
| | Total | 65.500 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 65.500 mg.

Example F

| | Weight based on a tablet containing 0.5 mg of roflumilast | |
|---|---|---|
| 1. | Roflumilast | 0.500 mg |
| 2. | Lactose monohydrate | 99.320 mg |
| 3. | Corn starch | 26.780 mg |
| 4. | Polyvidone K90 | 2.600 mg |
| 5. | Magnesium stearate (vegetable) | 1.300 mg |
| | Total | 130.500 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) in purified water is sprayed on and dried under suitable conditions. (5) is added to the granules, and the mixture obtained after mixing is compressed in a tablet press to tablets having an average weight of 130.5 mg.

Example G

| | Weight based on a tablet containing 2.5 mg of roflumilast | |
|---|---|---|
| 1. | Roflumilast | 2.500 mg |
| 2. | Microcrystalline cellulose | 33.900 mg |
| 3. | Corn starch | 2.500 mg |
| 4. | Polyvidone K90 | 2.250 mg |
| 5. | Sodium carboxymethylstarch (type A) | 20.000 mg |
| 6. | Magnesium stearate (vegetable) | 0.600 mg |
| | Total | 61.750 mg |

Production: (1) is mixed with part of (3), and a trituration is produced in a planetary mill. The trituration is put together with (2), (5) and the remaining amount of (3) in the product container of a fluidized bed granulation system, and a 5% granulation solution of (4) in purified water is sprayed on and dried under suitable conditions. (6) is added to the granules, and the mixture obtained after mixing is compressed in a tablet press to tablets having an average weight of 61.75 mg.

Example H

| | Production of tablets containing 0.1 mg of roflumilast as active ingredient (weight for a batch of 70000 tablets) | |
|---|---|---|
| 1. | Roflumilast (micronized) | 7.000 g |
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4557.000 g |

Production: (1) is mixed with 70 g of (3), and a trituration is produced in a planetary mill. The trituration is put together with (2) and the remaining amount of (3) in the product container of a fluidized bed granulation system, and a 5% granulation solution of (4) in purified water is sprayed on. (Spraying pressure: 3 bar; product temperature: 28-33° C.; air flow rate in the first third of the spraying process: 100 m$^3$/h; air flow rate subsequently during the spraying process: 150 m$^3$/h; inlet air temperature: 40-70° C.; spraying rate: 30-40 g/min). After spraying is complete, drying is carried out until the product temperature reaches 34° C. The granules are passed through a stainless steel sieve with a mesh width of 0.8 mm, and the relative surface moisture is measured and adjusted to a value in the range 20-50%. (5) is added to the granules, and the mixture obtained after mixing is compressed in a tablet press to tablets having an average weight of 65.1 mg.

Example I

| | Production of tablets containing 0.25 mg of roflumilast as active ingredient (weight for a batch of 70000 tablets) | |
|---|---|---|
| 1. | Roflumilast (micronized) | 35.000 g |
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4585.000 g |

Production: 19.25 g of (1) are mixed with 192.5 g of (3), and a trituration is produced in a planetary mill. The trituration is put together with (2) and the remaining amount of (3) in the product container of a fluidized bed granulation system, and a 5% granulation solution of (4) in purified water is sprayed on. (Spraying pressure: 3 bar; product temperature: 28-33° C.; air flow rate in the first third of the spraying process: 100 m$^3$/h; air flow rate subsequently during the spraying process: 150 m$^3$/h; inlet air temperature: 40-70° C.; spraying rate: 30-40 g/min). After spraying is complete, drying is carried out until the product temperature reaches 34° C. The granules are passed through a stainless steel sieve with a mesh width of 0.8 mm, and the relative surface moisture is measured and adjusted to a value in the range 20-50%. (5) is added to the granules, and the mixture obtained after mixing is compressed in a tablet press to tablets having an average weight of 65.5 mg.

Example J

| | Production of tablets containing 0.1 mg of roflumilast as active ingredient (weight for a batch of 70000 tablets) | |
|---|---|---|
| 1. | Roflumilast (micronized) | 7.000 g |
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4557.000 g |

Production: (1) is homogeneously suspended in a granulation solution of (4) in purified water. (2) and (3) are put into the product container of a suitable fluidized bed granulation system and granulated with the granulation suspension described above, and then dried. (5) is added to the granules, and the mixture obtained after mixing is compressed in a tablet press to tablets having an average weight of 65.1 mg.

Example K

| | Production of tablets containing 0.25 mg of roflumilast as active ingredient (weight for a batch of 70000 tablets) | |
|---|---|---|
| 1. | Roflumilast (micronized) | 35.000 g |
| 2. | Lactose monohydrate | 3476.200 g |
| 3. | Corn starch | 937.300 g |
| 4. | Polyvidone K90 | 91.000 g |
| 5. | Magnesium stearate (vegetable) | 45.500 g |
| | Total | 4585.000 g |

Production: (1) is homogeneously suspended in a granulation solution of (4) in purified water. (2) and (3) are put into the product container of a suitable fluidized bed granulation system and granulated with the granulation suspension described above, and then dried. (5) is added to the granules, and the mixture obtained after mixing is compressed in a tablet press to tablets having an average weight of 65.25 mg.

Example L

| | Weight based on a tablet containing 0.25 mg of roflumilast | |
|---|---|---|
| 1. | Roflumilast | 0.250 mg |
| 2. | Lactose monohydrate | 49.660 mg |
| 3. | Potato starch | 10.000 mg |
| 4. | Corn starch | 3.590 mg |
| 5. | PVP 25 | 1.500 mg |
| 6. | Magnesium stearate (vegetable) | 0.650 mg |
| | Total | 65.650 mg |

Production: A dispersion is produced from (4) and water, and (1) is homogeneously suspended therein. (5) is dissolved in water and added to the dispersion. (2) and (3) are granulated in a suitable fluidized bed granulation system with the dispersion under suitable conditions. (6) is added to this mixture, and the mixture obtained after mixing is compressed in a tablet press to tablets having an average weight of 65.650 mg.

Example M

| | Weight based on a tablet containing 0.25 mg of roflumilast | |
|---|---|---|
| 1. | Roflumilast | 0.250 mg |
| 2. | Lactose monohydrate | 49.660 mg |
| 3. | Corn starch | 13.390 mg |
| 4. | Polyvidone K90 | 1.300 mg |

-continued

| Weight based on a tablet containing 0.25 mg of roflumilast | | |
|---|---|---|
| 5. | Gelatin | 1.300 mg |
| 6. | Magnesium stearate (vegetable) | 0.650 mg |
| | Total | 66.550 mg |

Production: (1) is mixed with part of (3), and a trituration is produced in a planetary mill. The trituration is put together with (2) and the remaining amount of (3) in the product container of a fluidized bed granulation system, and a 5% granulation solution of (4) and (5) in purified water is sprayed on and dried under suitable conditions. (6) is added to the granules, and the mixture obtained after mixing is compressed in a tablet press to tablets having an average weight of 66.55 mg.

Example M1

Formulation for Pediatric Use

| Weight based on a tablet containing 0.125 mg of roflumilast | | |
|---|---|---|
| 1. | Roflumilast | 0.125 mg |
| 2. | Lactose monohydrate | 49.660 mg |
| 3. | Corn starch | 13.390 mg |
| 4. | Polyvidone K90 | 1.300 mg |
| 5. | Mannit | 32.238 mg |
| 6. | Flavor (Tutti Frutti) | 0.329 mg |
| 7. | PVP (Insoluble) | 12.895 mg |
| 5. | Magnesium stearate (vegetable) | 1.649 mg |
| | Total | 111.586 mg |

The formulation is produced according to a process disclosed above.

Physical Investigations and Comparative Tests with Dosage Forms in which No PVP was Used as Binder Example N The disintegration time and the release of active ingredient were determined for a dosage form corresponding to example D.

Disintegration time: the disintegration time was determined using a disintegration tester by the method described in the European Pharmacopoeia.

Result: 7.08 minutes.

Release of active ingredient: the release of active ingredient was determined as described in the US Pharmacopeia (USP XXV; apparatus 2).

Result: 78% of the active ingredient are released after 15 minutes, and quantitative release is observed after 60 minutes.

Example O

Production of a dosage form containing roflumilast in which no PVP is used:

| Weight based on a tablet containing 0.25 mg of roflumilast | | |
|---|---|---|
| 1. | Roflumilast | 0.250 mg |
| 2. | Lactose monohydrate | 70.300 mg |
| 3. | Potato starch | 19.475 mg |
| 4. | Corn starch | 3.563 mg |

-continued

| Weight based on a tablet containing 0.25 mg of roflumilast | | |
|---|---|---|
| 5. | Sodium carboxymethylstarch (Type A) | 1.900 mg |
| 6. | Magnesium stearate (vegetable) | 0.950 mg |
| | Total | 96.438 mg |

Production: A dispersion is produced from (4) and water, and (1) is homogeneously suspended therein. (2) and (3) are granulated in a suitable fluidized bed granulation system with the dispersion under suitable conditions. (5) is added to the dry granules, and a homogeneous mixture is produced. (5) is added to this mixture, and the mixture obtained after mixing is compressed in a tablet press to tablets having an average weight of 96.438 mg.

Comparative Study

Design: 24 subjects, 3-period changeover, randomized; dose in each case 0.5 mg (2 tablets each containing 0.25 mg of roflumilast). The serum concentration of roflumilast after oral administration of 0.5 mg (2 tablets each containing 025 mg) of roflumilast was investigated for the following dosage forms:

With PVP as Binder:

Tablet corresponding to example D, referred to as "treatment A" hereinafter.

Tablet corresponding to example K, referred to as "treatment B" hereinafter.

Without PVP as Binder:

Tablet corresponding to example O, referred to as "treatment C" hereinafter.

The results are depicted in FIG. 1. Higher serum levels were observed considerably more quickly after oral administration for dosage forms with PVP as binder compared with dosage forms without PVP. The rate of absorption is thus distinctly increased for the dosage forms of the invention.

INDUSTRIAL APPLICABILITY

The dosage forms of the invention can be employed for the treatment and prevention of all diseases regarded as treatable or preventable through the use of PDE 4 inhibitors. Selective cyclic nucleotide phosphodiesterase (PDE) inhibitors (specifically of type 4) are suitable on the one hand as bronchial therapeutic agents (for the treatment of airway obstructions owing to their dilating effect but also owing to their effect increasing the respiratory rate and respiratory drive) and for eliminating erectile dysfunction owing to the vasodilating effect, but on the other hand especially for the treatment of disorders, especially of an inflammatory nature, e.g. of the airways (asthma prophylaxis), of the skin, of the central nervous system, of the intestine, of the eyes and of the joints, which are promoted by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. The pharmaceutical preparations of the invention can therefore be used in human and veterinary medicine for example for the treatment and prophylaxis of the following diseases: acute and chronic (especially inflammatory and allergen-induced) airway disorders of various etiologies (bronchitis, allergic bronchitis, bronchial asthma, COPD); dermatoses (especially of a proliferative, inflammatory and allergic nature) such as, for example, psoriasis (vulgaris), toxic and allergic contact eczema, atopic eczema, seborrhoic eczema, lichen simplex, sunburn, pruritus in the genitoanal region, alopecia areata, hypertrophic scars, discoid lupus erythematosus, follicular and extensive pyodermas, endogenous and exogenous acne, acne rosacea and other proliferative, inflammatory and allergic skin disorders; disorders based on excessive release of TNF an leukotrienes, e.g. disorders of the arthritic type (rheumatoid arthritis, rheumatoid spondylitis, osteoarthritis and other arthritic states), disorders of the immune system (AIDS, multiple sclerosis), types of shock [septic shock, endotoxin shock, gram-negative sepsis, toxic shock syndrome and ARDS (adult respiratory distress syndrome)] and generalized inflammations in the gastrointestinal region (Crohn's disease and ulcerative colitis); disorders based on allergic and/or chronic abnormal immunological reactions in the region of the upper airways (pharyngeal space, nose) and adjacent regions (paranasal sinuses, eyes), such as, for example, allergic rhinitis/sinusitis, chronic rhinitis/sinusitis, allergic conjunctivitis and nasal polyps; but also cardiac disorders which can be treated by PDE inhibitors, such as, for example, heart failure, or disorders which can be treated owing to the tissue-relaxant effect of PDE inhibitors, such as, for example, erectile dysfunction or colic of the kidneys and ureters connected with kidney stones; or else disorders of the CNS such as, for example, depressions or arteriosclerotic dementia.

The invention further relates to a method for the treatment of mammals, including humans, suffering from one of the abovementioned diseases. The method is characterized by administration of a therapeutically effective and pharmacologically suitable amount of a PDE 4 inhibitor to the mammalian patient, the PDE 4 inhibitor being present in a dosage form of the invention. The disease is preferably asthma or airway obstructions, especially COPD (=chronic obstructive pulmonary disease).

The dosage forms of the invention comprise the PDE 4 inhibitor in the dose customary for the treatment of the particular disease. The dosage of the active ingredient is of the order of magnitude customary for PDE inhibitors, it being possible to administer the daily dose in one or more dosage units. The normal dose on systemic therapy (oral) is between 0.001 mg and 3 mg per kilogram and day. Dosage forms preferred according to the invention contain from 0.01 mg to 5 mg of roflumilast, preferably from 0.05 mg to 2.5 mg, particularly preferably 0.1 mg to 0.5 mg of roflumilast per dosage unit Examples of pharmaceutical preparations of the invention contain 0.1 mg, 0.125 mg, 0.25 mg and 0.5 mg of roflumilast per dosage unit. Normally, one or more than one dosage unit of the invention is administered once a day. If desired, it is also possible for one or more dosage units of the invention to be administered more than once a day.

The invention claimed is:

1. A dosage form for oral administration of a PDE 4 inhibitor produced by the process comprising the steps: (a) producing a mixture of a PDE 4 inhibitor of formula I

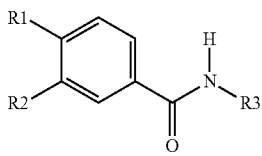

in which
R1 is difluoromethoxy,
R2 is cyclopropylmethoxy and
R3 is 3,5-dichloropyrid-4-yl,
or a salt of this compound, or an N-oxide of the pyridine of this compound or a salt thereof, and one or more pharmaceutical excipients;

and (b) granulating the mixture obtained in (a) with an aqueous solution of polyvinylpyrrolidone;
wherein the dosage form is in tablet or pellet form and wherein said dosage form provides immediate release of the PDE 4 inhibitor.

2. The dosage form of claim 1, further comprising:
(a) drying the granules,
(b) optionally admixing other pharmaceutical excipients,
(c) mixing with a release agent and
(d) compressing in a tablet press.

3. The dosage form according to claim 1; wherein the granulating takes place in a fluidized bed granulator.

4. The dosage form according to claim 1, wherein in step (a) the PDE 4 inhibitor is admixed with the one or more pharmaceutical excipients in the form of a trituration with a pharmaceutical excipient.

5. The dosage form according to claim 4, which trituration is obtained by grinding the PDE 4 inhibitor with the one or more pharmaceutical excipients.

6. The dosage form according to claim 4, wherein the pharmaceutical excipient is a filler.

7. The dosage form according to claim 1, comprising granulating a mixture of (a) a PDE 4 inhibitor of formula I, or a trituration of a PDE 4 inhibitor of formula I with corn starch, (b) corn starch and (c) lactose monohydrate with an aqueous polyvinylpyrrolidone solution to form granules, drying the granules, mixing the granules with a release agent and compressing the granules in a tablet press.

8. The dosage form according to claim 1, comprising granulating a mixture of (a) PDE 4 inhibitor of formula I, or a trituration of a PDE 4 of formula I with corn starch, (b) corn starch, (c) microcrystalline cellulose and (d) sodium carboxymethylstarch with an aqueous polyvinylpyrrolidone solution to form granules, drying the granules, mixing the granules with a release agent and compressing the granules in a tablet press.

9. A dosage form for oral administration of a PDE 4 inhibitor produced by the process comprising the steps:
(a) producing a mixture of pharmaceutical excipients; and
(b) granulating the mixture obtained in (a) with a suspension of a PDE 4 inhibitor of formula I,

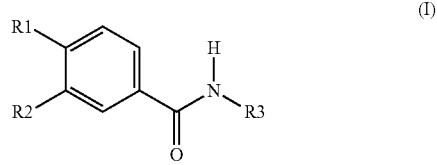

in which
R1 is difluoromethoxy,
R2 is cyclopropylmethoxy and
R3 is 3,5-dichloropyrid-4-yl
or a salt of this compound, or an N-oxide of the pyridine of this compound or a salt thereof, in an aqueous solution of PVP, wherein the dosage form is in tablet or pellet form and wherein said dosage form provides immediate release of the PDE 4 inhibitor.

10. The dosage form according to claim 9, comprising granulating a mixture of corn starch and lactose monohydrate with a suspension of a PDE 4 inhibitor of formula I in an aqueous solution of PVP to form granules, drying the granules, mixing the granules with a release agent and compressing the granules in a tablet press.

11. A dosage form for oral administration of a PDE 4 inhibitor produced by the process comprising the steps: (a) producing an active ingredient preparation in the form of a solid solution in polyvinylpyrrolidone of a PDE 4 inhibitor of formula I,

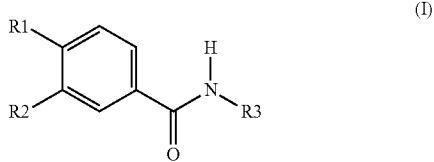

in which
R1 is difluoromethoxy,
R2 is cyclopropylmethoxy and
R3 is 3,5-dichloropyrid-4-yl,
or a salt of this compound, or an N-oxide of the pyridine of this compound or a salt thereof; (b) producing a mixture of an active ingredient preparation and pharmaceutical excipients and (c) granulating the mixture obtained in (b) with an aqueous solution of polyvinylpyrrolidone; wherein the dosage form is in tablet or pellet form and wherein said dosage form provides immediate release of the PDE 4 inhibitor.

12. The dosage form according to claim 9 in the form of a tablet, wherein the granules obtained in step (b) are dried, mixed with lubricants or release agents and compressed in a tablet press.

13. The dosage form according to claim 9 wherein the pharmaceutical excipient is a filler.

14. The dosage form according to claim 9, wherein the PVP is selected from the group consisting of polyvinylpyrrolidone of the weight average molecular weight 28,000-34,000, polyvinylpyrrolidone of the weight average molecular weight 44,000-54,000 and polyvinylpyrrolidone of the weight average molecular weight 1,000,000-1,500,000.

15. The dosage form according to claim 9, wherein the PDE 4 inhibitor is N-(3,5-dichloropyrid-4-yl)-3 cyclopropylmethoxy-4-difluoromethoxy benzamide (roflumilast).

16. The dosage form according to claim 9, wherein the PDE 4 inhibitor is the N-oxide of the pyridine of the compound of formula I.

17. The dosage form according to claim 10, containing from 0.01 mg to 5 mg of roflumilast per dosage unit.

18. The dosage form according to claim 9, wherein the proportion of polyvinylpyrrolidone is from 1 to 5% by weight.

19. The dosage form according to claim 9, wherein the proportion of polyvinylpyrrolidone is from 2 to 3% by weight.

20. The dosage form according to claim 9, where the pharmaceutical excipients are excipients selected from the group consisting of fillers, additional binders, tablet disintegrants, lubricants, release agents, flavouring substances, buffer substances, preservatives, coloring substances and emulsifiers.

21. The dosage form according to claim 9, wherein the proportion of all binders present is from 0.5 to 20% by weight.

22. The dosage form according to claim 20, which is a tablet and wherein the proportion of filler is from 40 to 99% by weight.

23. The dosage form according to claim 20, wherein the filler is selected from the group consisting of sugar alcohols, starches, saccharides and mixtures thereof.

24. The dosage form according to claim 23, wherein the filler is selected from the group consisting of corn starch, microcrystalline cellulose, lactose and mixtures thereof.

25. The dosage form according to claim 20, wherein the lubricant or release agent is selected from the group consisting of sodium stearyl fumarate, magnesium stearate, calcium stearate, stearic acid, talc and colloidal anhydrous silica.

26. The dosage form according to claim 9, wherein the pharmaceutical excipients are at least one filler and at least one lubricant or release agent.

27. The dosage form according to claim 9, comprising:
(a) Roflumilast 0.125 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

28. The dosage form according to claim 9, comprising:
(a) Roflumilast 0.250 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

29. The dosage form according to claim 9, comprising:
(a) Roflumilast 0.500 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

30. The dosage form according to claim 9, further comprising producing a solid solution of the PDE 4 inhibitor in the PVP as carrier.

31. The dosage form according to claim 30, wherein the solid solution is a solid solution with amorphous structure, in which the PDE 4 inhibitor is in the form of a molecular dispersion in the carrier material.

32. The dosage form according to claim 9, wherein said granulating step (b) is conducted in a fluidized bed granulator.

33. The dosage form according to claim 1, comprising:
(a) Roflumilast 0.125 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

34. The dosage form according to claim 1, comprising:
(a) Roflumilast 0.250 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

35. The dosage form according to claim 1, comprising:
(a) Roflumilast 0.500 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

36. The dosage form according to claim 11, comprising:
(a) Roflumilast 0.125 mg
(b) Lactose monohydrate 49.660 mg
(c) Corn starch 13.390 mg (d) Polyvinylpyrrolidone of the weight average molecular weight 1,000,000-1,500,000 1.300 mg; and
(e) Magnesium stearate (vegetable) 0.650 mg.

37. The dosage form according to claim 11, comprising:
(a) Roflumilast 0.250 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

38. The dosage form according to claim 11, comprising:
(a) Roflumilast 0.500 mg
(b) Lactose monohydrate 49.660 mg
(c) Corn starch 13.390 mg
(d) Polyvinylpyrrolidone of the weight average molecular weight 1,000,000-1,500,000 1.300 mg; and
(e) Magnesium stearate (vegetable) 0.650 mg.

* * * * *

UNITED STATES PATENT AND TRADEMARK OFFICE
CERTIFICATE OF CORRECTION

PATENT NO.        : 8,431,154 B2                      Page 1 of 3
APPLICATION NO.   : 13/008842
DATED             : April 30, 2013
INVENTOR(S)       : Rango Dietrich et al.

It is certified that error appears in the above-identified patent and that said Letters Patent is hereby corrected as shown below:

Title Page 4, Col. 1, Item (56) (Other Publications), on Line 18 delete "Roftumilast" and insert -- Roflumilast --, therefor.

Title Page 4, Col. 1, Item (56) (Other Publications), on Line 20 delete "Roftumilast" and insert -- Roflumilast --, therefor.

Title Page 4, Col. 1, Item (56) (Other Publications), on Line 23 delete ""Roftumilast," and insert -- "Roflumilast, --, therefor.

Title Page 4, Col. 1, Item (56) (Other Publications), on Line 26 delete ""Roftumilast," and insert -- "Roflumilast, --, therefor.

Title Page 4, Col. 1, Item (56) (Other Publications), on Line 30 "roftumilast," and insert -- roflumilast, --, therefor.

Title Page 4, Col. 1, Item (56) (Other Publications), on Line 32 delete ""Antiinftammatory" and insert -- "Antiinflammatory --, therefor.

Title Page 4, Col. 1, Item (56) (Other Publications), on Line 33 delete "Roftumilast," and insert -- Roflumilast, --, therefor.

Title Page 4, Col. 1, Item (56) (Other Publications), on Line 35 delete "anti-inftammatory" and insert -- anti-inflammatory --, therefor.

Title Page 4, Col. 1, Item (56) (Other Publications), on Line 36 delete "roftumilast"," and insert -- roflumilast", --, therefor.

Title Page 4, Col. 1, Item (56) (Other Publications), on Line 38-39 delete "Anti-Inflammatory-Inflammatory" and insert -- Anti-Inflammatory --, therefor.

Signed and Sealed this
Thirteenth Day of August, 2013

Teresa Stanek Rea
*Acting Director of the United States Patent and Trademark Office*

CERTIFICATE OF CORRECTION (continued)
U.S. Pat. No. 8,431,154 B2

Title Page 4, Col. 1, Item (56) (Other Publications), on Line 62 delete "Roftumilast"," and insert
-- Roflumilast", --, therefor.

Title Page 4, Col. 1, Item (56) (Other Publications), on Line 65 delete "Roftumilast" and insert
-- Roflumilast --, therefor.

Title Page 4, Col. 1, Item (56) (Other Publications), on Line 67 delete "Roftumilast" and insert
-- Roflumilast --, therefor.

Title Page 4, Col. 1, Item (56) (Other Publications), on Line 70 delete "Roftumilast" and insert
-- Roflumilast --, therefor.

Title Page 4, Col. 2, Item (56) (Other Publications), on Line 1 delete "Roftumilast" and insert
-- Roflumilast --, therefor.

Title Page 4, Col. 2, Item (56) (Other Publications), on Line 2 delete "Roftumilast-" and insert
-- Roflumilast- --, therefor.

Title Page 4, Col. 2, Item (56) (Other Publications), on Line 5 delete "Roftumilast" and insert
-- Roflumilast --, therefor.

Title Page 4, Col. 2, Item (56) (Other Publications), on Line 8 delete "Roftumilast," and insert
-- Roflumilast, --, therefor.

Title Page 4, Col. 2, Item (56) (Other Publications), on Line 16 delete "Lld." and insert
-- Ltd. --, therefor.

Title Page 4, Col. 2, Item (56) (Other Publications), on Line 18 delete "Roftumilast" and insert
-- Roflumilast --, therefor.

Title Page 4, Col. 2, Item (56) (Other Publications), on Line 27 delete "roftumilast" and insert
-- roflumilast --, therefor.

Title Page 4, Col. 2, Item (56) (Other Publications), on Line 29 delete ""Roftumilasl:" and insert
-- "Roflumilast: --, therefor.

Title Page 4, Col. 2, Item (56) (Other Publications), on Line 29 delete "Antialiergy/" and insert
-- Antiallergy/ --, therefor.

Title Page 4, Col. 2, Item (56) (Other Publications), on Line 33 delete "Roftumilast" and insert
-- Roflumilast --, therefor.

Title Page 4, Col. 2, Item (56) (Other Publications), on Line 37 delete "Roftumilast" and insert
-- Roflumilast --, therefor.

CERTIFICATE OF CORRECTION (continued)
U.S. Pat. No. 8,431,154 B2

Title Page 4, Col. 2, Item (56) (Other Publications), on Line 41 delete "PDE4lnhibitor" and insert -- PDE4 inhibitor --, therefor.

Title Page 4, Col. 2, Item (56) (Other Publications), on Line 49 delete "roftumilast" and insert -- roflumilast --, therefor.

Title Page 4, Col. 2, Item (56) (Other Publications), on Line 50 delete "inftammation" and insert -- inflammation --, therefor.

Title Page 5, Col. 1, Item (56) (Other Publications), on Line 36 delete "o" and insert -- of --, therefor.

Title Page 5, Col. 1, Item (56) (Other Publications), on Line 51 delete "Therapeuctics" and insert -- Therapeutics --, therefor.

Title Page 5, Col. 1, Item (56) (Other Publications), on Line 56 delete "(Engilsh" and insert -- (English --, therefor.

In the Specifications

Column 1, Line 10 (approx.) delete "02004811.3," and insert -- 02003811.3, --, therefor.